United States Patent
Husain

(10) Patent No.: US 6,187,973 B1
(45) Date of Patent: Feb. 13, 2001

(54) GLYCOL PURIFICATION

(75) Inventor: Mansoor Husain, Berkeley Heights, NJ (US)

(73) Assignee: Scientific Design Company, Inc., Little Ferry, NJ (US)

( * ) Notice: Under 35 U.S.C. 154(b), the term of this patent shall be extended for 0 days.

(21) Appl. No.: 09/544,029

(22) Filed: Apr. 6, 2000

(51) Int. Cl.[7] .......................... C07C 29/74; C07C 27/26; C07C 31/22
(52) U.S. Cl. .......................... 568/870; 568/871; 568/872
(58) Field of Search .................................... 568/870, 871, 568/872

(56) References Cited

U.S. PATENT DOCUMENTS

| | | |
|---|---|---|
| 3,904,656 | 9/1975 | Broz . |
| 4,349,417 | 9/1982 | Rebsdat et al. . |
| 4,358,625 | 11/1982 | Paggini et al. . |
| 4,560,813 | 12/1985 | Collier . |
| 5,440,058 | 8/1995 | Hoffman et al. . |

FOREIGN PATENT DOCUMENTS 2558039   7/1976   (DE) .

OTHER PUBLICATIONS

Database CAPLUS on STN, Acc. No. 1995:220402, Schmitt et al, 'Purification of ethylene glycol using anion exchange resins.' CA 1330350 A1 (abstract), 1995.*

* cited by examiner

Primary Examiner—Samuel Barts
Assistant Examiner—Brian J. Davis
(74) Attorney, Agent, or Firm—William C. Long

(57) ABSTRACT

Aqueous ethylene glycol solution containing aldehydes such as formaldehyde, acetaldehyde and the like is contacted with a solid bisulfite treated strong base anion exchange resin and a solution reduced in aldehydes content is separated.

2 Claims, No Drawings

GLYCOL PURIFICATION

BACKGROUND OF THE INVENTION

1. Field of the Invention

The present invention relates to the removal of impurities such as aldehydes from aqueous ethylene glycol solutions by treatment with bisulfite treated strong base anion exchange resin.

2. Description of the Prior Art

Ethylene glycol is a very important chemical of commerce which is usually prepared by reaction of ethylene oxide and water. A problem which has existed is that during the preparation procedure impurities such as aldehydes are formed which are difficult to separate from ethylene glycol and which cause problems in applications where very high purity is required, for example in the manufacture of fibers.

Both physical methods as well as chemical methods have been devised for the separation of aldehydes from ethylene glycol. U.S. Pat. No. 4,349,417, for example, proposes distillation in the presence of a alkali metal compounds as a purification procedure. This patent also refers to German Ausligeschrift No. 2,558,039 as teaching ethylene glycol purification using an ion exchange resin.

U.S. Pat. No. 4,358,625 teaches reducing oxygen—containing impurities by treatment with alkali metal borohydride.

U.S. Pat. No. 3,904,656 teaches treating a purge stream from an ethylene oxide stripper with a cation exchange resin Amberlyst A-15, an anion exchange resin Amberlyst A-21, and a carbon bed prior to recycle.

U.S. Pat. No. 4,560,813 teaches hydrolysis of alkylene oxide using a methylate anion—containing natural and recovery of the methylate anion by contact with a solid such as anion exchange resin.

U.S. Pat. No. 5,440,058 mentions treatment of aqueous streams with weakly basic ion exchange resins which have been reacted with a bisulfite salt in order to remove aldehyde impurities.

Despite the efforts of prior workers, further improvements in the removal of impurities such as aldehydes from aqueous ethylene glycol streams is important and desirable.

BRIEF DESCRIPTION OF THE INVENTION

In accordance with the invention, an aqueous ethylene glycol stream which contains aldehyde impurity is contacted with a bisulfite treated strong base anion exchange resin and an aqueous ethylene glycol stream reduced in aldehyde content is recovered.

DETAILED DESCRIPTION

Strong base anion exchange resins are used in the process of the invention. Prior to contact with the impure aqueous glycol stream to be treated, the resins are first converted to the bisulfite form by contact with a bisulfite solution such as aqueous sodium bisulfite. Other bisulfites can, of course, be used. In the bisulfite treatment the strongly basic anion resin is converted to the bisulfite form in accordance with the following:

resin-OH$^-$+Na$^+$HSO$^-_3$ solution–resin-HS$^-_3$+Na$^+$OH$^-$ solution

Aqueous ethylene glycol solution containing aldehyde such as formaldehyde or acetaldehyde is then contacted with the bisulfite treated solid resin and an aqueous ethylene glycol solution reduced in content of aldehydes is separated from the solid resin.

While not intending to be bound by theory, it is believed that during contact of the bisulfite treated strongly basic resin and solution, aldehyde undergoes reactive ion exchange on the resin as follows:

resin-HSO$^-_3$+HCHO solution–resin-HOCH$_2$SO$^-_3$ in effect binding the aldehyde to the solid resin and thus removing it from solution.

Treatment in accordance with the invention provides an efficient and effective method for removal of aldehydes from aqueous ethylene glycol solution. By monitoring the aldehydes content of the effluent stream, it can easily be determined when the solid resin should be regenerated. This regeneration is conveniently carried out by contacting the spent resin with an aqueous bisulfite solution in accordance with the following:

resin-HOCH$_2$SO$^-_3$+Na$^+$HSO$^-_3$ solution–Na$^+$HOCH$_2$SO$^-_3$ solution+resin-HSO$^-_3$.

Generally speaking, the aqueous solutions treated in accordance with the invention comprise about 0.2 to 20 wt % ethylene glycol, about 80 to 99.7 wt % water and about 100 ppm to 1.0 wt % aldehydes. The ethylene glycol solution is contacted with the bisulfite treated resin at moderate temperatures, eg. about 30 to 50° C. although temperatures outside this range can be used. Atmospheric pressure is preferred but higher pressures can be used. Illustrative flow rates are about 1 to 10 volumes of solution per volume of resin per hour although this can vary widely.

Ion exchange resins which are employed in practice of the invention are strongly basic anion exchange resins which are well known articles of commerce.

The strong-base resins can be produced by the reaction between chlormethylated styrene-DVB copolymer and a tertiary amine such as trimethyl amine, which results in a resin with quaternary ammonium groups.

A comprehensive description of strong base anion exchange resin suitable for use herein and their preparation can be found in Kirk-Othmer, Encyclopedia of Chemical Technology, 5th Edition, Vol 14 pages 747–749 (1990).

The following examples illustrate the invention:

A strong base anion exchange resin was converted to the bisulfite form by passing a 5 wt % aqueous solution of sodium bisulfite through a bed of the resin until the bisulfite inlet and outlet concentrations were essentially the same. The resin employed was TULSION A-33, a cross-linked polystyrene which contained quaternary ammonium groups in hydroxide form. The resin was then washed with 10–15 volumes of water per volume of resin.

A synthetic ethylene glycol solution comprised of 1 wt % formaldehyde and the rest water was passed through the bisulfite treated resin at 35° C. After 5 volumes of solution were treated by the resin per volume of resin, the outlet solution formaldehyde concentration was below 2 ppm.

The above example was repeated using an actual monoethylene glycol process stream comprised of 5 wt % monoethylene glycol and 95 wt % water and containing 150 ppm of total aldehyde. As a result of the contact the total aldehydes content was reduced to 1 ppm in the effluent stream.

I claim:

1. The method for reducing the aldehydes content of an aqueous aldehydes-containing ethylene glycol solution comprised of about 0.2 to 20 wt % ethylene glycol; about 80 to 99.7 wt % water and about 100 ppm to 1.0 wt % aldehydes which comprises contacting the solution with a solid bisulfite treated strong base anion exchange resin having quaternary ammonium functional groups in hydroxide form before bisulfite treatment.

2. The method of claim 1 wherein the bisulfite is sodium bisulfite.

* * * * *